United States Patent [19]

Liese et al.

[11] Patent Number: 4,566,438

[45] Date of Patent: Jan. 28, 1986

[54] FIBER-OPTIC STYLET FOR NEEDLE TIP LOCALIZATION

[76] Inventors: Grover J. Liese, 1301 Punch Bowl St., Honolulu, Hi. 96813; William Pong, 3317 Huelani Dr., Honolulu, Hi. 96822

[21] Appl. No.: 658,312

[22] Filed: Oct. 5, 1984

[51] Int. Cl.$^4$ .............................................. A61B 1/06
[52] U.S. Cl. .......................................... 128/6
[58] Field of Search ........................................ 128/4, 6

[56] References Cited

U.S. PATENT DOCUMENTS

| | | | |
|---|---|---|---|
| 2,699,770 | 1/1955 | Fourestier et al. | 128/6 |
| 2,932,294 | 4/1960 | Fourestier et al. | 128/6 |
| 3,349,762 | 10/1967 | Kapany | 128/6 X |
| 3,556,085 | 1/1971 | Takahashi | 128/6 |
| 3,961,621 | 6/1976 | Northeved | 128/6 X |
| 4,269,192 | 5/1981 | Matsuo | 128/6 X |

OTHER PUBLICATIONS

Johannah Medical Services advertisement for "The Percutaneous Transhephatic Cholangiography (PTC) Chiba 'Skinny' Needle", Jun. 1, 1979.
Advertisement for Chiba Needle Trays.
Advertisement for Greene Biopsy Needle Trays.
Applied Optics, Sep. 1964, vol. 3, No. 9, pp. 1031 and 1032, entitled "The Fiber-Optics Hypodermic Microscope", by Charles Long et al.
Nature, Aug. 26, 1961, No. 4791, at pp. 927 and 928.

*Primary Examiner*—William H. Grieb
*Attorney, Agent, or Firm*—Sandler & Greenblum

[57] ABSTRACT

A fiber-optic stylet is provided for use with a surgical or diagnostic type needle. The stylet comprises an elongated flexible or rigid casing which is adapted to be inserted into the body of a human or animal. It also includes at least one transmitting light fiber having a bevelled end which extends to a first end of the casing and that conforms to that of the needle. A second, receiving light fiber has a bevelled end and is also positioned within the casing, also having its bevelled end located at the first end of the needle. The second fiber-optic element is generally cylindrical and has a reflective surface thereon which is located adjacent to the bevelled end of the light fiber. The apparatus is used to precisely determine the area in which a needle is positioned within a body during a diagnostic or surgical procedure.

24 Claims, 6 Drawing Figures

FIBER-OPTIC STYLET FOR NEEDLE TIP LOCALIZATION

BACKGROUND OF THE INVENTION

1. Field of the Invention

The present invention generally relates to needles used in percutaneous diagnostic and therapeutic procedures, and more specifically to needles incorporating fiber-optic stylets which are provided to localize placement of the tip of the needle during surgical and medical diagnostic procedures.

2. Information Disclosure

In medical radiology, long, slender or skinny needles have been inserted into various body organs through the skin for a variety of purposes, e.g., to obtain tissue for biopsy from probable tumor masses such as from the lungs, kidneys, pancreas, or liver, to cannulate liver ducts by percutaneous transhepatic cholangiography, or to pierce the kidney pelvis in preparation for a percutaneous nephrostomy in order to treat blocked ureters.

Despite the use of preliminary measuring procedures such as ultrasound and CT scanning, and the use of fluoroscopy, it is extremely difficult, if not impossible, for a doctor or technician to determine the positional relationship of the tip of a needle to an internal organ or part of an organ to be treated. In the case of percutaneous transhepatic cholangiography, for example, a needle is inserted deep into a liver and is slowly retracted while small doses of contrast material are injected to determine whether the needle tip is properly positioned within the liver duct system. The needles used in these procedures have metal stylets, which fill the needle so that the needle is essentially solid as it traverses the body as it moves towards its final position. This prevents bits of tissue from entering the tube of the needle, and undesirably results in "blocked" needles.

NORTHEVED, U.S. Pat. No. 3,961,621, discloses a device capable of taking biological samples from a human body. The device comprises an elongated bevel-cut tubular needle, a tubular stiletto having a sharp edged distal end, a core of optical fibers, and bundles of light conducting fibers. The stiletto covers the fiber bundles, which are evenly distributed within a space located between a core of the device and the stiletto tube wall. Spaces between the fiber bundles serve as air ducts in order to create a partial vacuum which cause the sample collected to adhere to the distal end of the device. The fiber bundles guide light from an exterior source to an interior surface of the body, and the core of guiding light fibers reflect the light back to an external display unit. In order to collect a biological sample, a partial vacuum is applied to cause the stiletto to slide forwardly through the needle and into abutment with an interior surface of the body. The distal end of the stiletto cuts out a biological sample, which due to the vacuum applied adheres to the distal end of the needle.

MATSUO, U.S. Pat. No. 4,269,192, discloses a device for diagnosing illness. The device comprises a tubular member having a bevel-cut end, light guiding means, and a photosensitive device. The light guiding means are inserted into the tubular member, and both of the tip ends are bevel-cut to match the level that of the end portion caps of the tubular member. The end-portion caps are inserted into the examination area using the light guide in order to admit light into the examination area through the front end of the tip. Light is reflected from the examination area and then admitted into the light guide fiber through the front end, thus activating an LED by the photosensor. The intensity of light reflected and signalled by the LED indicates the exact location of the end-position caps of the member.

TAKAHASHI, U.S. Pat. No. 3,556,085, discloses an optical viewing device which comprises a bevel-cut fiber-optic system, a magnifying objective lens system, a fiber-optic viewing system, a magnifying eye piece, and an illuminating system. The device is inserted into a living body for direct examination of interior surfaces, and the tip of the fiber-optic system is inserted into a body and illuminated by the system. The magnifying system and an eyepiece are used to examine an area of interest, and the lens system can be variously positioned in order to obtain different types of magnification.

FOURESTIER, U.S. Pat. No. 2,432,294, discloses a lighting device for endoscopes which comprises a transparent rod having a plurality of reflective surfaces for guiding light to an interior region of a body to be observed. The transparent rod is contained within a sheath to guard against humidity, and a space is filled with dry air and separates the sheath from the rod. In cases where lateral illumination is desired, the sheath can be bevel-cut. The rod can also be bevel-cut, but need not extend to the tip of the sheath.

None of these patents, however, disclose the use of a reflective surface layer on a receiving optical fiber which is adapted to redirect incoming light back to a light sensor and an analyzer. The reflective layer increases the precision of the analysis which can be performed.

OBJECTS OF THE INVENTION

Accordingly, it is a general object of the present invention to provide a new and improved fiber-optic stylet for needle tip localization which overcomes all of the above-noted deficiencies of the prior art.

A further object of the present invention is to provide a new and improved fiber-optic stylet for use in a surgical or diagnostic needle which has a plurality of optical fibers incorporated within it, at least one of which transmits light to the tip of the needle, and the other of which brings reflected light to a light sensor and to a light color and intensity analyzer.

Another object of the present invention is to provide a new and improved fiber-optic stylet for use with a surgical or diagnostic needle which is adapted to reflect incoming light and redirect it towards a receiving fiber.

Still another object of the present invention is to provide a new and improved fiber-optic stylet for use with a surgical or diagnostic needle which incorporates a light sensor, a light analyzer, and/or a television or other display screen to determine the intensity and color of reflected light in order to localize the needle tip.

Still a further object of the present invention is to provide a new and improved fiber-optic stylet for a surgical or diagnostic needle which can replace a stylet entirely with optical fibers mounted in plastic or other relatively stiff material in order to provide a stylet having both sufficient flexibility and longitudinal strength.

A further object of the present invention is to provide a new and improved fiber-optic stylet for use with a surgical or diagnostic needle which will clearly indicate whether the tip of the needle is in contact with blood, bile, or a membrane wall, and to further identify the area near the tip of the needle.

Other objects and advantages of the present invention will become more fully apparent to others of ordinary skill in the art which this invention pertains from review of the following detailed description, drawings and claims.

SUMMARY OF THE INVENTION

The present invention comprises a fiber-optic stylet for use with a diagnostic or surgical type needle. The stylet comprises an elongated flexible or rigid casing adapted to be inserted into body and has a first end and a second end. It also includes a first, transmitting fiber-optic means which comprises at least one transmitting light fiber which has a bevelled end which extends to the first end of the casing. Receiving fiber-optic means are also provided and comprise at least one receiving light fiber having one bevelled end which extends to the first end of the casing. The bevelled ends of the two fibers are positioned adjacent the first end of the flexible casing. The receiving light fiber is generally cylindrical and has a reflective surface thereon which is located adjacent to the bevelled end of the receiving light fiber. The reflective surface coats only about the lowest one-half of the generally cylindrical receiving fiber and only in the area adjacent the bevelled fiber end. A needle is positioned about the casing and has a bevelled end which generally corresponds to the bevelled ends of the two fibers, all of the bevelled ends being substantially coextensive. The casing can be made of either metal or plastic, and the needle is adapted to fit over and around the first end of the casing. The bevel of the receiving and transmitting fibers generally matches the bevel of the needle.

The receiving fiber, and its reflective layer, comprises means for redirecting light reflected from a body area being examined to the second end of the receiving fiber, towards a user of the assembly. Each of the fiber-optic means can comprise more than one fiber, and an eyepiece can be attached to the receiving fiber at a second end of the fiber. Both fibers can extend beyond the second casing end. The reflective layer preferably comprises a thin film of aluminum which is vapor-deposited onto the surface of the receiving fiber. The device can be used in combination with a light intensity and color analyzer and a display for displaying the results of the analysis. The light analyzer can be a monochromator or a spectrophotometer. The light analyzer can alternately comprise a micro-computer having analogue to digital conversion capability and which comprises means for rapidly analyzing the color and intensity of all of the light reflected from the body area being analyzed. The metallic needle can comprise, e.g., stainless steel. The tip of the casing is bevelled and is preferably sealed with a low vapor pressure epoxy.

The transmitting fiber-optic means is connected to a light source which may be a 300-watt zenon light source. Other light sources may be employed as well, i.e., laser or ultraviolet sources. Infrared and light could be used as a heat source as well. The receiving fiber-optic means is connected to a magnifying pocket microscope. A water cell and a quartz lens are positioned adjacent to the light source and to the transmitting fiber(s). The receiving light fiber preferably has a larger diameter than the transmitting fiber.

BRIEF DESCRIPTION OF THE DRAWINGS

The above and other objects, features and advantages of the present invention will become more fully apparent to those of ordinary skill in the art to which this invention pertains from the following detailed description, the attached claims, and the accompanying drawings, in which like reference numerals are used to describe like parts throughout the several views, and wherein:

DETAILED DESCRIPTION OF THE DRAWINGS

Figure 1:
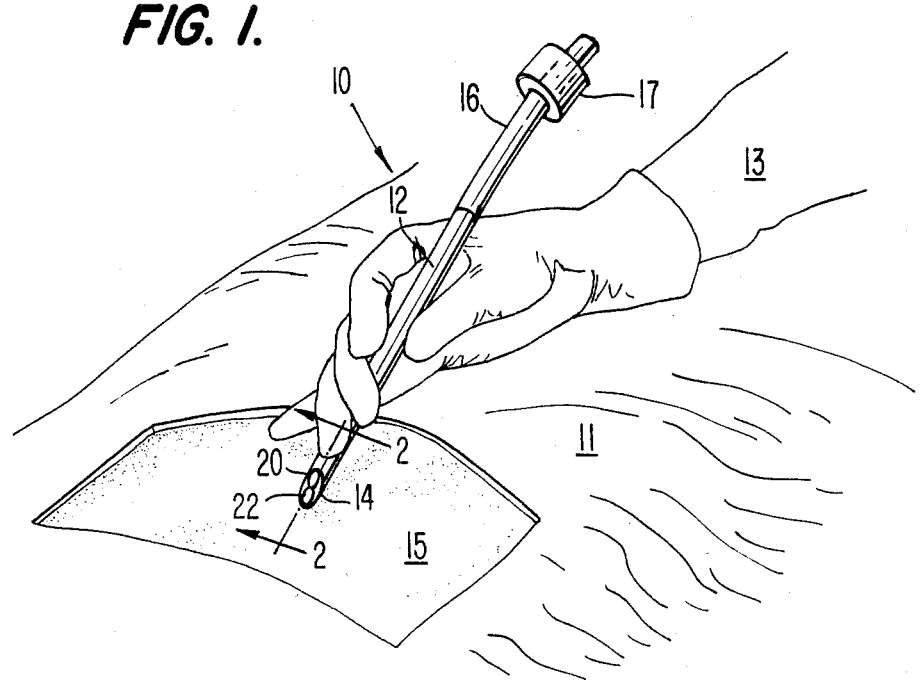
FIG. 1 is a perspective view of a physician inserting a needle incorporating the fiber-optic stylet of the present invention into a selected body portion.

Referring more specifically to the drawings, FIG. 1 illustrates the hand 13 of a doctor or other user using a combination needle and stylet assembly 10 formed in accordance with the present invention. Needle 12 incorporates a bevelled tip or end 14 which is adapted to be inserted into the human body and positioned adjacent an area to be viewed. Flexible casing 16 is surrounded by the needle and is positioned at its first end within the generally cylindrical needle 12. A wound or other incision 15 is shown in body 11, and although arm 13 is shown as inserting the needle, the needle could equally well be at the end of casing 16 which has been inserted through the throat of a patient or from a distant insertion point, the hand of an operator then being located away from the area of incision. The needle has a diameter on the order of less than one millimeter. It is illustrated in FIG. 1 as being larger, however, to facilitate consideration of this application.

Figure 2:
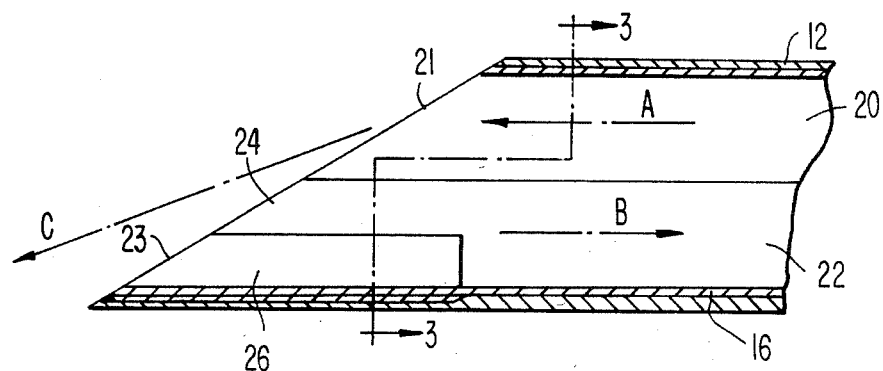
FIG. 2 is a sectional view taken along line 2—2 of FIG. 1, illustrating the stylet in cross section.
Figure 3:
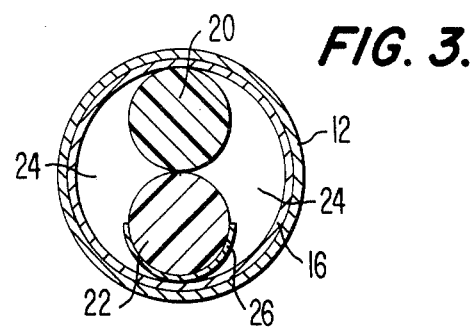
FIG. 3 is a sectional view taken along line 3—3 of FIG. 2 illustrating a front sectional view of the stylet and needle of FIG. 1.

The first end of the stylet is illustrated in FIG. 1; stylet casing 16, which is generally cylindrical, is preferably formed from either flexible metal, e.g., 22 gauge surgical stainless steel, or plastic. The first casing end is positioned within needle 12, and the front portion 14 of needle 12 and the first end of casing 16 are bevelled in a similar fashion. Both the needle and stylet can include hubs (illustrated at 17) to facilitate handling. The bevelled end of casing 16 is sealed by a low vapor pressure epoxy, in order to form a clear yet secure surface 24. Positioned within tubular casing 16, and running at least along the entire extent thereof, are transmitting and receiving fibers 20 and 22, respectively, as shown in FIGS. 2 and 3. The fibers can be longer than the casing and may therefore extend beyond the second casing end. The transmitting optic fiber 20 transmits light from a light source (illustrated in FIG. 5) through a lens 27 and a water cell 28 to the fiber-optic element 20.

As illustrated in FIG. 2, both light fibers 20 and 22 have bevelled front surfaces, 21 and 23 respectively, which essentially mate with the bevelled front surface 14 of the needle and the bevelled front surface of the tubular casing 16, which is sealed by epoxy 24. Epoxy is placed adjacent the fibers within the bevelled end of casing 16, as shown in FIG. 3. The arrows A and B in FIGS. 2, 4, and 5 all indicate the direction in which light is travelling through the elements. As best shown in FIG. 3, lower fiber 22 has a reflective coating, e.g., an aluminum coating 26 which extends over essentially half of the cylindrical periphery of the fiber, but preferably only in an area adjacent the bevelled fiber end 23 (see FIG. 2). The advantages of such a coating will be explained hereinafter.

As noted previously, the present stylet is adapted to replace previously used metal stylets. The optical fibers which are incorporated within the center of casing 16 are provided to transmit light to the tip of the stylet (i.e., transmitting fiber element 20) and to then bring scattered, reflected and fluorescent light back to a sensor (i.e., receiving fiber-optic element 22). Because bevelling results in incoming light being reflected away from the tip of the optical fiber, the reflective aluminum layer 26 is provided to redirect light towards receiving fiber 22.

The fiber-optic stylet is slideably positioned within needle 12, and is adapted to be placed into the needle when the tip of the needle is near a desired position or area in the body of a patient to be examined. Light, including ultraviolet light, can be directed through one or more fibers in fiber-optic element 20 (either of the fiber-optic elements can be either a single fiber or a bundle of fibers), and thereafter either scattered or fluorescent light will be conducted through receiving fiber or fibers 22 and observed with an eyepiece at a second fiber end, distant from the bevelled fiber end. The light reflected from the body area is then passed through analyzing equipment, where both intensity and color of the reflected light will be used to help localize the needle tip. Fluorescent measurements can also be taken to assist in localization, dependent upon the fluorescence of the biological materials which are exposed to ultraviolet light.

Although the casing 16 is preferably formed from metal, suitable plastic materials which are flexible, yet stiff enough to provide suitable longitudinal strength can also be used. Use of the fiber-optic stylet can be adopted for both humans and animals, and can be used to determine whether the needle tip is in contact with blood, bile and/or in close proximity to the light reflective intima of a blood vessel or bile duct.

Such sophisticated localization is extremely helpful when used in conjunction with percutaneous diagnostic and therapeutic procedures which arise during conventional hospital radiologic practice.

Figure 4:
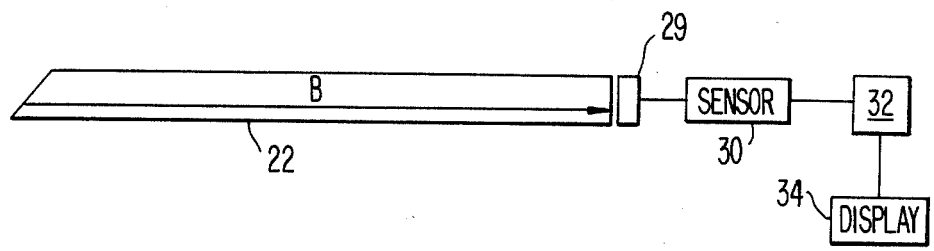
FIG. 4 is a block diagram of the overall system including the stylet and needle of the present invention, together with the indicators and analyzers illustrated by appropriate blocks.
Figure 5:
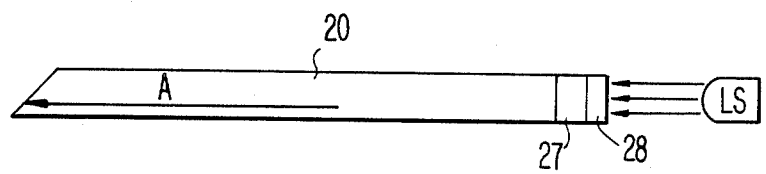
FIG. 5 is a plan view of the elements (illustrated by blocks) which are attached to the receiving light fiber.

One preferred embodiment of the stylet is one which is adapted to fit within an 18-gauge hypodermic wide spinal needle, the needle being approximately 9 centimeters long. The stylet preferably contains two optical fibers, as illustrated in FIG. 3, which are sealed within a stainless steel tube 16 having a wall thickness of approximately 0.15 millimeters. The bevelled end of the stylet, as discussed previously, is sealed with a low vapor pressure epoxy that can be heated to 250° F. The tip of the stylet is bevelled to conform in shape to the tip of the needle (as are the "combined" bevelled ends of fibers 20 and 22), and can thus be easily cleaned and polished. The opposite, or first end of the stainless steel casing or cylinder is used to provide support for bare fibers and for the external fiber shield. The transmitting fiber is connected to a light source, as shown in FIG. 5; one embodiment of a suitable light source is a 300-watt xenon light source. Light from the xenon source passes through a water cell 28 to a quartz lens 27, which is adapted to focus light on the second end of transmitting fiber 20. The receiving fiber 22 can be connected to a microscope 29 such as shown in the block diagram of FIG. 4.

The fibers are arranged within the stylet in order to enhance emergence of light from the bevel-cut end of the receiving fiber. As illustrated in FIG. 2 by arrow C, light can come out of the transmitting fiber 20 at a variety of angles, dependent upon the relative refractive indices of the fiber and the fluid or solid body area which is in contact with the bevel-cut face of the fiber. If the bevelled end of the fiber is positioned in a fluid, e.g., water, the light will appear more intense near the apex, and it will come out at an angle of approximately 70 degrees with respect to a line which is perpendicular to the bevelled face. For this reason, incoming light or transmitting fiber 20 is positioned over receiving-light fiber 22, as illustrated best in FIG. 3. This will maximize the light received (and thus transmitted) by light fiber 22.

The optical response of the receiving fiber can be improved by placing a reflective aluminum surface 26 over approximately half the lower cylindrical surface of the fiber near its tip. It is preferred that the diameter of the receiving fiber be greater than the diameter of the transmitting fiber in order to maximize transmission in fiber 22. In one embodiment, the diameter of the incoming-light transmitting fiber is approximately 140 micrometers, whereas the diameter of the receiving light fiber is approximately 240 micrometers. The optical fibers are adapted to transmit ultraviolet light having wave lengths above 2000 Å or 200 nm.

Figure 6:
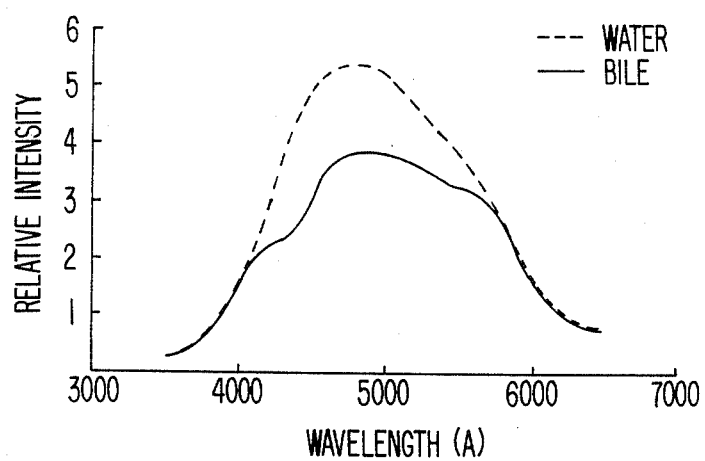
FIG. 6 is a graph illustrating the relative response of the assembly when the tip is positioned in water and bile, respectively.

In order to investigate color response of this stylet, applicants have inserted a needle having the fiber-optic stylet into solutions of various colors. The color of scattered light received at the bevelled end of the receiving fiber was clearly manually distinguishable at the opposite end through the microscope. The spectral intensity of scattered light received by the optical fiber at the tip of the stylet was measured with a grating monochromator. The receiving fiber of the stylet was connected directly to the entrance slit of the monochromator. The dispersed light from the exit slit of the monochromator was detected with a photomultiplier tube (PMT) cooled with boiling liquid nitrogen. The relative response at different wavelengths when immersing the needle with the stylet into water and into bile is well illustrated in the graph of FIG. 6. As can be seen from the graph, the intensity of scattered light from bile is lower than that of water in the blue and green regions of the spectrum. The spectral response of the PMT is lower in the longer wavelength regions.

Light scattered from water appears as white to the human eye, whereas light scattered from bile appears to be brown to the human eye; the spectral response detected with a PMT is consistent with the colors seen by the human eye, and the relative responses of water and bile illustrated shows the same intensity in the violet, yellow and red regions, whereas the bile response shows a lower intensity than water in the blue and green regions. Thus, suppression of the blue and green intensity in the white light spectrum will account for the brown color of bile viewed.

The use of a needle using the present fiber-optic stylet has been demonstrated by performing a percutaneous transhepatic cholangiography on an anesthetized animal, and applicants were able to clearly identify blood and bile when the needle tip made contact with the respective biological fluids. As the needle tip approaches a bile duct or blood vessel wall, scattered white light will become more intense. When the needle tip is fixed at a predetermined position within a gall bladder region near the membrane wall, slight movement caused by breathing of the anesthetized animal produces an alternating color change of white and yellow-brown. Such a color change will enable a doctor or other technician to accurately position the needle tip when performing these and other diagnostic tests, as well as during surgical procedures.

Reflective layer 26 is attached to the appropriate portion of the surface of fiber 22 by coating the cylindrical surface of the fiber with a thin film of aluminum. The aluminum is vapor-deposited in a vacuum and is condensed in the form of a thin film on the fiber surface. Use of the reflective film provides an advantage in obtaining a greater percentage of reflective light than is obtainable without such a film. Part of an overall system incorporating the stylet assembly 10 of the present invention are illustrated in FIG. 4. As shown in FIG. 4, a sensor 30 is adapted to receive light transmitted by receiving fiber element 22. In this case, the microscope (29) is replaced by the monochromator. The sensor then sends a signal to a suitable microcomputer 32, e.g., a microcomputer capable of analog to digital conversion and which can provide rapid analysis of the color and intensity of reflected light. A display 34 can also be provided to facilitate analysis.

An intense laser source (illustrated) can be provided to photoexcite biological molecules within the human body in which a needle is inserted, and in order to observe the photoreponse of the molecules as a function of wave length and time. Light collected by the receiving fibers can be transmitted to a light intensifier which is capable of distinguishing the color of light received. The color of light detected by the receiving fiber can be viewed on a color television screen. The television screen, laser source and light intensifier are all well-known items which could be represented by black boxes if desired in this application. They have not presently been illustrated because they are considered to be substantially conventional.

The embodiments of the invention disclosed above have been used for illustrative purposes only, and it is apparent that there are modifications and equivalents of the present invention which would be within the skill of those with ordinary skill in the art.

What is claimed is:

1. A fiber-optic stylet for use with a diagnostic or surgical needle, said stylet comprising:
   (a) an elongated casing adapted for insertion into a body, said casing having a first end and a second end;
   (b) transmitting fiber-optic means comprising at least one transmitting light fiber having one bevelled end extending adjacent said first casing end;
   (c) receiving fiber-optic means comprising at least one receiving light fiber having one bevelled end extending adjacent said first casing end, wherein said bevelled end of said transmitting light fiber and said bevelled end of said receiving light fiber are positioned at the same end of said flexible casing; and
   (d) wherein said receiving light fiber is generally cylindrical and has a reflective surface thereon which is located adjacent to said bevelled end of said receiving light fiber and said first casing end.

2. A fiber-optic stylet in accordance with claim 1 wherein said reflective surface is positioned over only approximately one-half of the periphery of said receiving light fiber, and only along a portion of said receiving fiber which is adjacent to said bevelled end of said receiving fiber.

3. A fiber-optic stylet in accordance with claim 1 further comprising a generally tubular needle surrounding said first end of said casing, said needle having a bevelled end generally corresponding in shape to said bevelled end of said casing.

4. A fiber-optic stylet in accordance with claim 3 wherein said first casing end is bevelled, the bevelled ends of said light fibers are substantially coextensive with the bevelled end of said casing, and the bevelled end of said casing is substantially coextensive with the bevelled end of said needle.

5. A fiber-optic stylet in accordance with claim 1 wherein said casing is metallic.

6. A fiber-optic stylet in accordance with claim 5 wherein said casing is stainless steel.

7. A fiber-optic stylet in accordance with claim 2 wherein said receiving light fiber and said reflective layer comprise means for directing light reflected from a body area being examined to a distal, second end of said receiving fiber.

8. A fiber-optic stylet in accordance with claim 1 wherein each of said fiber-optic means comprises a plurality of optical fibers.

9. A fiber-optic stylet in accordance with claim 1 wherein an eyepiece is attached to a second end of said receiving light fiber, and wherein both of said fibers extend beyond said second end of said casing.

10. A fiber-optic stylet in accordance with claim 9 further comprising a light analyzer and a display.

11. A fiber-optic stylet in accordance with claim 10 wherein said light analyzer is a monochromator.

12. A fiber-optic stylet in accordance with claim 10 wherein said light analyzer is a spectrophotometer.

13. A fiber-optic stylet in accordance with claim 10 wherein said light analyzer comprises a computer with analog and digital conversion capability, said computer comprising means for rapidly analyzing the color and intensity of light reflected from a body area adjacent to the bevelled end of said fibers.

14. A fiber-optic stylet in accordance with claim 1 wherein said casing is plastic.

15. A fiber-optic stylet in accordance with claim 1 wherein said reflective layer is a thin film of aluminum which is vapor-deposited on the surface of said receiving fiber.

16. A fiber-optic stylet in accordance with claim 1 wherein said casing has a tip which is bevelled and which is sealed with a low vapor pressure epoxy.

17. A fiber-optic stylet in accordance with claim 1 wherein said transmitting fiber-optic means is connected to a light source.

18. A fiber-optic stylet in accordance with claim 17 wherein said light source is a 300-watt xenon light source.

19. A fiber-optic stylet in accordance with claim 17 further comprising a water cell and a quartz lens positioned adjacent to said light source and to said transmitting optical fiber.

20. A fiber-optic stylet in accordance with claim 1 wherein said receiving fiber-optic means is connected to a microscope.

21. A fiber-optic stylet in accordance with claim 1 wherein said receiving light fiber has a diameter which is larger than the diameter of said transmitting light fiber.

22. A fiber-optic stylet in accordance with claim 1 further comprising an intense laser source which comprises means for photoexciting biological molecules within a human body and means for observing the photoresponse of the molecules as a function of wave length and time.

23. A fiber-optic stylet in accordance with claim 18 further comprising means for transmitting light collected by said receiving light fiber and further comprising a light intensifier for distinguishing the color of light received by said fiber.

24. A fiber-optic stylet in accordance with claim 23 further comprising a color-television screen for determining the color of light detected by said receiving fiber.

* * * * *